United States Patent [19]
Sawyer et al.

[11] Patent Number: 5,749,895
[45] Date of Patent: *May 12, 1998

[54] METHOD FOR BONDING OR FUSION OF BIOLOGICAL TISSUE AND MATERIAL

[75] Inventors: Philip N. Sawyer, Brooklyn, N.Y.; Donald G. Wallace, Menlo Park; Ronald K. Yamamoto, San Francisco, both of Calif.

[73] Assignee: Fusion Medical Technologies, Inc., Mountain View, Calif.

[*] Notice: The term of this patent shall not extend beyond the expiration date of Pat. No. 5,156,613.

[21] Appl. No.: 303,336

[22] Filed: Sep. 6, 1994

Related U.S. Application Data

[63] Continuation-in-part of Ser. No. 7,691, Jan. 22, 1993, abandoned, which is a continuation-in-part of Ser. No. 832,171, Feb. 6, 1992, abandoned, which is a continuation-in-part of Ser. No. 654,860, Feb. 13, 1991, Pat. No. 5,156,613.

[51] Int. Cl.$^6$ ............................................. A61B 17/04
[52] U.S. Cl. ..................... 606/214; 606/8; 606/213; 606/40; 606/154
[58] Field of Search .................. 424/400; 606/7, 606/8 R, 10, 12, 17, 213 R, 214, 40 R, 3, 215, 153, 154 R, 155, 32; 128/898

[56] References Cited

U.S. PATENT DOCUMENTS

| | | | |
|---|---|---|---|
| 2,011,169 | 8/1935 | Wappler | 128/303.14 |
| 2,510,205 | 6/1950 | Baird | 219/8 |
| 2,618,267 | 11/1952 | Hanriot | 128/303.14 |
| 2,708,933 | 5/1955 | August | 128/303.14 |
| 2,808,833 | 10/1957 | Augard | 128/303.17 |
| 3,527,224 | 9/1970 | Rabinowitz | 606/214 |
| 3,578,939 | 5/1971 | Green | 219/74 |
| 3,742,955 | 7/1973 | Battista | 606/214 |
| 3,834,392 | 9/1974 | Lampman et al. | 128/303.13 |
| 3,858,586 | 1/1975 | Lessen | 128/303.1 |

(List continued on next page.)

FOREIGN PATENT DOCUMENTS

| | | |
|---|---|---|
| 330 135 | 8/1989 | European Pat. Off. . |
| 405 429 | 2/1991 | European Pat. Off. . |
| 91/04073 | 4/1991 | WIPO . |
| 92/02238 | 2/1992 | WIPO . |

OTHER PUBLICATIONS

Oz et al. (1990). SPIE vol. 1200 (Progress in Biomedical Optics), pp. 55–59.

Costello et al., "Sutureless End–to–End bowel Anastomosis Using Nd:YAG and Water–Soluble Intraluminal Stent," (1990), *Laser in Surgery and Medicine*, vol. 10, pp. 179–184.

Poppas et al., "Laser Welding in Urethral Surgery: Improved Results with a Protein Solder," (1988), *J. Urology*, vol. 139(2), pp. 415–417.

(List continued on next page.)

*Primary Examiner*—Raj Bawa
*Attorney, Agent, or Firm*—Townsend and Townsend and Crew LLP

[57] ABSTRACT

Biological materials are joined, repaired or fused by heating the material in proximity to a mechanical support. Preferably, the mechanical support comprises a patch or bridge structure. In the most preferred embodiment, the patch is formed from collagen having a thickness from between 2 to 30 mils, and most preferably from 2 to 15 mils thick. Preferably, the patch or support structure contains holes or interlock vias which permit the coagulum to form a mechanical bond therewith, whether preformed or generated by an electrical energy source during welding. The preferred method comprises the steps of: first, placing the patch in contact with the materials to be joined, supplying energy to the tissue in an amount sufficient to form a coagulum at the surface of the patch, and finally, permitting the coagulum to form a mechanical bond with the support or patch. The preferred energy source is an inert gas beam RF energy source, with the preferred gas being argon, and the preferred energy range from about 3 to 80 watts. Support structures are utilized in connection with the welding of collapsible structures.

10 Claims, 8 Drawing Sheets

U.S. PATENT DOCUMENTS

| | | | |
|---|---|---|---|
| 3,903,891 | 9/1975 | Brayshaw | 128/303.14 |
| 3,991,764 | 11/1976 | Incropera | 128/303.1 |
| 4,040,426 | 8/1977 | Morrison | 128/303.17 |
| 4,060,088 | 11/1977 | Morrison et al. | 606/303.17 |
| 4,100,390 | 7/1978 | Jackson | 219/74 |
| 4,122,853 | 10/1978 | Smith | 128/303.1 |
| 4,238,480 | 12/1980 | Sawyer | 424/177 |
| 4,618,885 | 10/1986 | Nagasaki | 358/98 |
| 4,638,800 | 1/1987 | Michel | 606/14 |
| 4,640,279 | 2/1987 | Beard | 128/303.14 |
| 4,672,969 | 6/1987 | Dew | 606/3 |
| 4,708,137 | 11/1987 | Tsukagoshi | 128/303.15 |
| 4,733,660 | 3/1988 | Itzkan | 606/17 |
| 4,781,175 | 11/1988 | McGreery et al. | 128/303.7 |
| 4,854,320 | 8/1989 | Dew et al. | 128/397 |
| 4,878,492 | 11/1989 | Sinofsky et al. | 128/303.1 |
| 4,889,120 | 12/1989 | Gordon | 606/7 |
| 4,892,098 | 1/1990 | Sauer | 606/8 |
| 4,901,719 | 2/1990 | Trenconsky et al. | 606/49 |
| 4,901,720 | 2/1990 | Bertrand | 606/40 |
| 4,929,246 | 5/1990 | Sinofsky | 606/3 |
| 4,930,504 | 6/1990 | Diamantopoulas et al. | 606/3 |
| 4,943,290 | 7/1990 | Rexroth et al. | 606/45 |
| 5,002,051 | 3/1991 | Dew | 606/12 |
| 5,021,452 | 6/1991 | Labbé et al. | 514/474 |
| 5,041,110 | 8/1991 | Fleenor | 606/34 |
| 5,071,417 | 12/1991 | Sinofsky | 606/8 |
| 5,140,984 | 8/1992 | Dew et al. | 606/11 |
| 5,209,776 | 5/1993 | Ban et al. | 606/214 |

OTHER PUBLICATIONS

Barry et al., "The Effect of Radiofrequency–Generated Thermal Energy on the Mechanical and Histologic Characteristics of the Arterial Wall in Vivo," Rad. Ang., vol. 117, No. 2, pp. 332–341, Feb. 1989.

Bass et al., "Anastomosis of Biliary Tissue with High–Frequency Electrical Diathermy," Surgical Endoscopy, vol. 4, No. 2, pp. 94–96 (1990).

Bass et al., "Sutureless Microvascular Anastomosis Using the THC:YAG Laser: a Preliminry Report," Microsurgery, vol. 10, pp. 189–193 (1989).

Becker et al., "Radiofrequency Balloon Angioplasty Rationale and Proof of Principle", Invest. Rad., vol. 23, No. 11, pp. 810–817, 1988.

Benke et al., "Comparative Study of Suture and Laser–Assisted Anastomoses in Rat Sciatic Nerves," Lasers in Surgery and Medicine, 9:602–615 (1989).

Chemical Abstracts, vol. 114, No. 5, 38993y (1990).

Chuck et al., "Dye–Enhanced Laser Tissue Welding", Lasers in Surgery and Medicine, vol. 9, pp. 471–477 (1989).

Dennis et al., Evaluation of Electrofulguration in Control of Bleeding of Experimental Gastric Ulcers, Digestive Diseases and Sciences, vol. 24, No. 11, pp. 845–848, Nov. 1979.

Hendry et al., "Argon Beam Coagulation Compared with Cryoablation of Ventricular Subendocardium," Ann. Thorac. Surg. vol. 55, pp. 135–139, 1993.

Komerska et al., "Collagen Films as Test Surfaces for Skin—Contact Pressure Adhesives," 1990.

Lee et al., Thermal Compression and Molding of Atherosclerotic Vascular Tissue with Use of Radiofrequency Energy, JACC vol. 13, No. 5, pp. 1167–1175, Apr. 1989.

Libutti et al., "Canine Colonic Anastomoses Reinforced with Dye–Enhanced Fibrinogen and a Diode Laser", Surgical Endoscopy, vol. 4, No. 2, pp. 97–99 (1990).

Oz et al., "A Fiberoptic Compatible Midinfrared Laswer with $CO_2$ Laser–like Effect: Application to Atherosclerosis," Journal of Surgical Research, vol. 17, No. 6, pp. 439–501 (1989).

Oz et al., "Effects of a 2.15 –Micron Laser on Human Atherosclerotic Xenograft in Vivo", Angiology, The Journal of Vascular Diseases, vol. 41, pp. 772–776 (1990).

Oz et al., "In Vitro Comparison of Thulium–Holmium–Chromium: YAG AND Argon Ion Lasers for Welding of Biliary Tissue," Lasers in Surgery and Medicine, vol. 9, pp. 248–253 (1989).

Oz et al., "Strength of Laser Vascular Fusion: Preliminary Observations on the Role of Thrombus," Lasers in Surgery and Medicine, vol. 10, pp. 3939–395 (1990).

Oz et al., "Tissue Soldering by Use of Indocyanine Green Dye–Enhanced Fibrinogen with the Near Infrared Diode Laser," Journal of Vascular Surgery, vol. 11, No. 5, pp. 718–725 (1990).

Pachence et al., "Collagen: Its Place in the Medrail Device Industry," Jan. 1987.

Popp et al., "Welding of Gallbladder Tissue with a Pulsed 2.15 μm Thulium–Holmium–Chromium:YAG Laser," Lasers in Surgery and Medicine, 9:155–159 (1989).

Shapiro et al., "Microvascular End–To–Side Arterial Anastomosis Using the ND;YAG Laser," Neurosurgery, vol. 25, No. 4(1989) pp. 584–589.

Treat et al., "Preliminary Evaluation of a Pulsed 2.15 μm Laser System for Fiberoptic Endoscopic Surgery," Lasers in Surgery and Medicine, vol. 8, pp. 322–326 (1988).

METHOD FOR BONDING OR FUSION OF BIOLOGICAL TISSUE AND MATERIAL

RELATED APPLICATION INFORMATION

This application is a continuation-in-part of application Ser. No. 08/007,691, filed Jan. 22, 1993, now abandoned, which is a continuation-in-part of application Ser. No. 07/832,171, filed Feb. 6, 1992, now abandoned, which is a continuation-in-part of application Ser. No. 07/654,860, filed Feb. 13, 1991, now U.S. Pat. No. 5,156,613.

FIELD OF THE INVENTION

The present invention relates to the reattachment, joining, bonding or fusion of biological materials. Most particularly, it relates to tissue welding and bonding, utilizing a weldable support structure.

BACKGROUND OF THE INVENTION

The medical arts have utilized various techniques throughout the years in an effort to reattach or bond biological materials. For example, sutures have long been used to hold tissues in adjoining apposition to promote repair and provide hemostasis. More recently, other mechanical structures such as staples have been used towards a similar end.

Particularly useful are reconstructive materials which are biodegradable and integrate with the body over time, eliminating the adverse reactions with a chronic foreign body. Stabilized collagen "gut" sutures have been used early in medicine, followed by modern biodegradable synthetic polymers used for sutures and staples.

For certain types of procedures, additional mechanical securement materials are used in conjunction with the sutures and/or staples. For example, polypropylene mesh patches have been used in connection with tissue repair and reconstruction procedures to distribute mechanical loads, especially useful in load bearing applications such as in hernia repair. The use of a biodegradable patch for visceral surgery has been suggested in Tayot et al, U.S. Pat. No. 5,201,745 entitled "Visceral Surgery Patch". Specifically, Tayot discloses a patch of two layers of collagen superimposed and closely combined consisting of a porous adhesive layer of fibrous collagen sponge, which is relatively thick, and a second layer of dense collagen and/or gelatin film. In use, the wound to be closed is held in close apposition with the adhesive fibrous collagen material, with securement effected by either the use of a biological glue or by clot formation and integration into the porous sponge which apposes the tissue. No other means of patch securement is described.

Beyond mechanical measures, various "welding" or cauterizing procedures have been used. For example, electrosurgery has been used in which biological tissues or materials are placed in adjoining apposition and are cauterized or melted to form a coagulum. Radio frequency (RF) energy has been utilized in both uni-polar and bi-polar generators to attempt to "weld" or "solder" biological tissue.

Further, optical energy, in particular that generated by lasers, has been applied and utilized in the medical field for similar surgical purposes. A typical use of laser cauterization is described in U.S. Pat. No. 4,122,853. Various prior uses of lasers or other sources are described in Sawyer U.S. Pat. No. 5,156,613, incorporated herein by reference.

U.S. Pat. No. 4,672,969 discloses one method and apparatus for utilizing laser emitted optical energy to effect wound closure or other reconstruction of biological tissue by applying the optical energy to produce thermal heating of the biological tissue to a degree suitable for denaturing the tissue proteins such that the collagenous elements of the tissue form a "biological glue" which seals the tissue following cooling to effect the joining. This "glue" is later reabsorbed by the body during the healing process. The patent discloses a number of different types of lasers with preference stated for the ND:YAG type, because its particular wavelength allows optical energy to propagate without substantial attenuation through water and/or blood for absorption in the tissue to be repaired.

Despite these modifications, however, the weakness of the weld joint still remains the primary disadvantage of tissue welding procedures. Extensive current research is being conducted in an attempt to improve on that deficiency. U.S. Pat. No. 5,156,613 and application Ser. No. 07/832,171 each disclose the use of filler material, such as collagen, to improve the strength of the weld joint.

In addition to mechanical and welding methods for tissue reconstruction, tissue adhesives have also been investigated. While there are many high strength industrial adhesives, they typically either do not provide adhesion in the biological environment or they are too toxic for such use. Biological glues utilizing fibrin polymerization, for example, provide a nontoxic, flowable material which sets into a solid. However, these glues tend to have low adhesive strength and are more suitable for use as a biological sealant after mechanical securement means. Fibrin, fibrinogen glue and albumin used to "glue" tissues also present a problem in that such materials obtained from pooled plasma are potentially contaminated with Hepatitis and HIV viruses.

Despite the great desirability of an improved technique for high strength reattachment or fusion of biological materials, no wholly satisfactory solution has been proposed prior to this invention and application which are related to it.

SUMMARY OF THE INVENTION

Biological materials are joined, repaired or fused by heating the material in proximity to a mechanical support. In the preferred embodiment, the mechanical support comprises a patch or bridge structure. In the most preferred embodiment, the patch is formed from collagen having a thickness from between 2 to 30 mils. The patch may include either biologically degradable materials or biologically non-degradable materials, or both in combination. A resultant mechanically stable bond is formed with the patch and the underlying tissue, providing large bonding area resulting in a high strength repair.

The overall method according to this invention comprises the steps of: first, placing the patch in contact with the tissues to be joined, supplying energy to the tissue in an amount sufficient to form a coagulum at the surface of the patch, permitting the coagulum with cooling to form a mechanical bond with the support or patch.

Preferably, the patch or support structure contains holes or interlock vias which permit the coagulum to form a mechanical bond therewith. If the patch does not have holes prior to tissue application, an energy source, preferably an RF inert gas energy source, such as an argon beam coagulator may be utilized to concurrently create small holes while providing heat for the welding operation. Alternatively, the patch may be formed with holes prior to application, this being particularly useful for patches having a low electrical conductivity or relatively substantial thickness. Surprisingly, the use of such holes, either produced prior to welding or during the welding operation, provides not only mechanical fixation, but also provides a fluid and gas seal due to the sealing of the pores during welding.

In the preferred embodiment, a collagen patch is used with an RF inert gas energy source. Preferably, the patch is of a thickness from 2 to 30 mils, with an energy source from about 3 to 80 watts, with the inert gas being preferably argon or helium. Alternatively, energy from a standard electrosurgery device may be used.

The weldable support structures of this invention are preferably formed from biodegradable materials which integrate with the underlying tissue and tissue components such as coagulum upon application of the welding energy. The preferred biodegradable materials include collagen, gelatin, elastin, fibrinogen, albumin, and composites and add mixtures thereof. The mechanical properties of the weldable support structures may be increased by incorporating higher strength mechanical materials, including non-biodegradable materials, as a reinforcing mesh or by particle loading. Preferably, the support structure does not separate, or lose mechanical integrity upon application of the welding energy. Such materials include various high strength degradable materials such as polylactic/glycolic acid mesh or highly cross-linked collagen or gelatin woven mesh. High strength, non-degradable materials useable in a composite provide a support for a surrounded matrix of degradable, weldable material. Non-degradable material meeting the structural and functional requirements of the invention include porous polytetrafluoroethylene (PTFE), polypropylene mesh (Marlex), and polyester fabrics such as Dacron, or other materials conventionally sutured into place.

In another aspect of this invention, support elements are utilized in connection with the welding of collapsible structures. For example, an expandable stent is located within a collapsible structure, such as a bowel, and expanded against the interior of the structure prior to the welding of the patch. Once the weld is completed, the stent may be collapsed and removed. Alternatively, an absorbable stent, such as a gelatin stent, can be placed in the interior of the structure for support, and after use, absorbed.

Collagen patches having varying thickness may be utilized with this invention provided that sufficient energy is transferred through the patch to the underlying tissue to form coagulum. Thick collagen patches, up towards 30 mils may be utilized wherein the edges of the patch or structure are tacked down prior to providing energy to the patch interior. Thinner patches, with a thickness from substantially 2 to 15 mils, may be attached by directly bathing the patch in energy. Advantageously, the energy may be applied or transferred through the thinner patch, allowing bonding of substantially the entire patch area, while providing a gas and liquid tight seal.

It is an object of this invention to provide for improved reattachment or fusion of biological materials.

It is yet a further object of this invention to reduce healing time in connection with biological welding or tissue fusion.

BRIEF DESCRIPTION OF THE DRAWINGS

FIGS. 2(a), (b), (c) and (d) show various layouts of collagen gel to form patches, FIGS. 2(a) and (b) showing a generally parallel configuration and FIGS. 2(c) and (d) showing a generally radial configuration.

DETAILED DESCRIPTION OF THE INVENTION

Figures 1A, 1B, 1C:
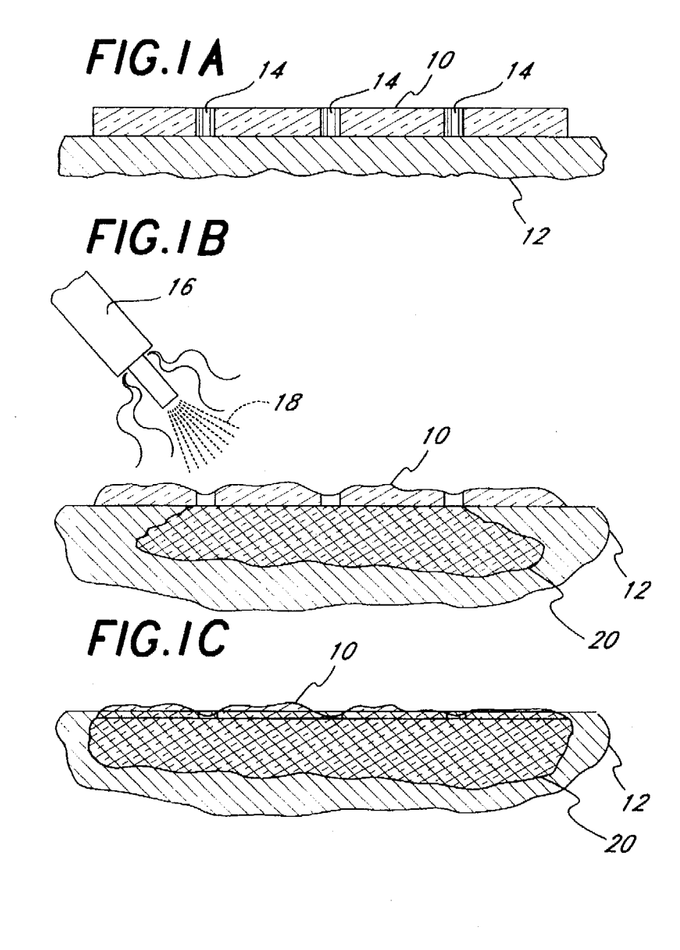
FIGS. 1(a)–(c) show cross-sectional drawings of a patch and tissue.

FIG. 1 provides a cross sectional view of a patch 10 in contact with tissue 12. In FIG. 1(a), the patch 10 is shown placed adjacent the tissue 12 prior to application of energy. In the embodiment shown, the patch 10 has preformed holes for interlock vias 14. Such holes need not be preformed in the patch 10, but are advantageously included in certain embodiments. In FIG. 1(b), an energy source 16 provides a blanket of energy 18 directed towards the patch 10 and tissue 12. The energy plume 18 causes the formation of a coagulum 20 in the tissue 12 beneath the patch 10. Preferably, the coagulum flows through the holes or interlock vias 14 in the patch 10. FIG. 1(c) shows the state after the coagulum has cooled. The patch 10 provides a mechanical support for the coagulum 20. Advantageously, the coagulum in the holes or interlock vias 14 provides further mechanical strength for the tissue 12. In one aspect of this invention, the patch may be formed of collagen, which, when heated, can denature with the tissue causing a coagulum upon cooling. A mechanical interlock arrangement results.

The term patch is used to include various structures, including but not limited to a structure having a greater extension in two dimensions relative to a third (e.g., thickness) dimension. Alternatively, the term may be used to describe other structures having a thickness component sized similar to another dimension, such as a tube or rod-shaped structure.

The patch or fusible structure 10 is subject to a number of general requirements. First, the patch should have sufficient strength after welding to provide mechanical support so as to hold the tissue in place while the healing process proceeds. Generally, the patch should last for a period of time sufficient to provide medical benefit, often 3–5 days, with that time on occasion being upwards of 60 days. Second, as to heat sensitivity, the patch optimally should substantially survive the heating by the energy plume 18, subject to the formation of the holes or interlock vias 14. Generally, it is desirable to survive heating to at least 160–170 F., but more preferable to survive to the boiling point of water. A third aspect of the patch is the electrical conductivity. In one aspect of this invention, a patch having good electrical conductivity permits the energy to go through the patch to form a coagulum 20 beneath the patch 10.

In one aspect of this invention, the patch or fusible structure 10 has holes or interlock vias 14 formed in the patch 10. The holes may be created during the application of the energy plume 18 such as by the action of an electrical discharge. This technique is particularly advantageous when the patch has sufficient electrical conductivity to permit passage of the energy from the patch through to the tissue 12. Alternatively, the patch may have holes formed prior to its application. The holes then comprise interlock vias 14 which are adapted to permit the coagulum 20 to form a mechanical bond with patch 10. Generally, the preforming of holes or interlock vias 14 is desirable when the patch 10 has a relatively low electrical conductivity, so that the energy plume 18 cannot easily form holes in the patch 10. The holes should be sized sufficiently to permit the coagulum 20 provide effective interlock with the patch 10. In the preferred embodiment, the range of sizes of the holes or interlock vias is 5μ to 3 mm. Generally, the space between the holes or interlock vias 14 should be such that the electrical discharge arc contained within the energy plume 18 may go from one interlock via 14 to the next, without arcing to a structure other than an interlock via 14. Such a distance is typically in the range of 5μ to 3 mm. Preformed holes or interlock vias 14 are particularly important for relatively thick patches 10, such as when thickness is greater than 15 mils, and/or patches 10 having relatively high electrical resistivity and/or a relatively high melting point, such as materials having a melting point over substantially 100 C. Generally, the use of holes or interlock vias 14 may be formed either as discrete holes or as a mesh structure.

The hydration of a patch material prior to welding also has an effect on energy transfer to the underlying tissue substrate. Overly hydrated materials tend to convert the applied energy into localized generation of steam, limiting energy transfer and coagulum formation by the tissues needed to form an adhesive bond. Materials with extremely high fluid absorption capacity, such as a thick foam, reduce the effectiveness of the patch welding. Hydrophobic coatings to limit hydration have some use in controlling the hydration effect.

Biocompatibility is yet another consideration in patch choice. Preferably, the patch 10 is a material which will not cause inflammation, toxicity, or adverse immune response, both before and after any potential chemical conversion due to the welding procedure. However, inflammatory materials may be used consistent with the invention herein.

In the preferred embodiment, a patch 10 formed from collagen is used. Most preferably, one or more collagens are used which are compatible, although any collagen compatible with use in the body may be employed. Generally, the collagen patch 10 should be thin enough to permit the energy plume 18 to transmit energy to the tissue 12, and thin enough to result in formation of holes or interlock vias 14. The collagen patch 10 is preferably thick enough to provide sufficient structural strength both to promote healing after the procedure and maintain apposition of tissue in the weld. Generally, the collagen patches 10 fall into three thickness ranges, generally considered to be thin from 0.5 mils to 7 mils, medium from 7 to 15 mils and thick from 15 to substantially 30 mils. The medium patches are the most preferred, but the thin for certain lung welds and thick for tendon welds have particular suitability. The medium thickness patches ranging from substantially 7 to substantially 15 mils in thickness are thick enough to provide sufficient mechanical strength yet thin enough to permit good energy conduction and to readily form holes for interlock vias 14 by action of electrical discharge. The relatively thin patches in the range up to substantially 7 mils provide sufficient strength for certain applications. Thicker patches may be utilized with or without preformed holes. In the event the patch is sufficiently thick such that electrical discharge cannot form holes, and no preformed holes exist, a weld or fusion may be made with the edges of the patch 10 and the tissue 12.

The collagen patch may be formed from any technique which provides a patch which functions to provide the derived features of this invention. For example, the method described by Chu, et al, in U.S. Pat. No. 4,725,671 could be used to form collagen films of appropriate thickness. Generally, this method consists of utilizing a relatively low viscosity, low percent solid collagen solution which is neutralized, heated and then compressed to form a higher density film. The steps for forming this collapsed collagen gel film are as follows:

1. Type 1 soluble collagen is formed into an aqueous solution or dispersion. Such collagen is available from Collagen Corporation, Palo Alto, Calif. and Kensey-Nash Corp., Exton, Pa.

2. The soluble collagen is cast as a gel. Type 1 collagen (described in Grillo and Gross, J. Surg. Res. 2, 1962, pp. 69–82) at 2–6 mg protein/ml in dilute acid (e.g., 0.01MHCL) is chilled to 2–5 C. Sodium chloride, sodium phosphate, and sodium hydroxide are added to the chilled solution to achieve approximately 0.13M sodium chloride, 0.020M sodium phosphate, pH 7.0 or near neutrality. The chilled solution is raised to about 37 C. and held 16–24 hours. The collagen will form a gel during incubation if it has sufficient native structure.

3. The gel is compressed into a film, with sufficient force to displace the water and allow for collapsing of the gel without gel fracture. The compressed gel is washed in water to reduce salt levels and then optionally in plasticizer, such as 1% sorbitol (weight per volume) to increase film flexibility.

4. The compressed film is dried, preferably in a low temperature oven or incubator, or simply by air drying at room temperature, at relatively low relative humidity.

5. The dried films are then cut into appropriately sized patches, packaged and sterilized for medical use.

However, films fabricated from compressed gels tend to exhibit tremendous residual stress, which is inherent in the non-uniform compression method. Such stresses could deform the patch during use, especially during releasing of such anisotropic stresses with the application of the welding thermal energy. In particular with collagen materials, the inherent shrinkage of the film upon thermal conversion to gelatin may also produce adverse deformation of the film caused by film non-uniformity. Collagen, when thermally denatured to gelatin, will contract near the melting point of the collagen triple helix, typically between 35 to 70 degrees centigrade. The resultant deformation of the patch when excessive, inhibits welding due to curling of the film and loss of tissue apposition. The patch shrinkage and curling is accentuated by increased water content of the patch during welding which reduces the thermal conversion threshold.

A preferred method of fabricating a collagen film with controlled thermal deformation properties involves the orientation of the collagen polymer chains in a planar direction. This oriented film appears to control the deformation by minimizing the perpendicular alignment of the polymer chains and resultant deformation in the non-planar direction. In one embodiment, the film is cast from a relatively high concentration gel of non-fibrillar collagen material at a fairly high concentration. The preferred method utilizes the following steps.

1. Type 1 collagen at from about 0.5 to 20 mg protein per ml was placed in dilute acid (e.g., 0.01M HCl) and was precipitated by addition of sodium hydroxide and sodium phosphate to achieve a final pH of 6.9 to 8.8 and a phosphate concentration of 0.01 to 0.03M. Precipitation can be effected by rapid addition of sodium phosphate and sodium hydroxide as concentrated solutions, followed by stirring.

2. The flocculated collagen was harvested, by centrifugation to yield a concentrated, opaque fibrous gel from approximately 35 to 70 mg protein per ml, depending on the centrifugal force applied.

3. The gel was acidified, by chilling to approximately 2 to 5 C., at which time acid, such as 0.1N hydrochloric acid was added in small volume increments with stirring to achieve a transparent, non-fibrillar collagen gel or solution at approximately 20–40 mg per ml.

4. The acidified gel was then neutralized, through the addition of sodium hydroxide and sodium phosphate to achieve 0.092 to 0.15M sodium chloride and 0.01 to 0.03M sodium phosphate at a pH of from substantially 7.0 to 8.8. The still chilled, non-fibrillar collagen at this stage was extremely viscous and transparent.

5. Optionally, air bubbles were removed from the gel, preferably by centrifugation.

6. The gel was then formed into films.

Figures 2A, 2B, 2C, 2D:
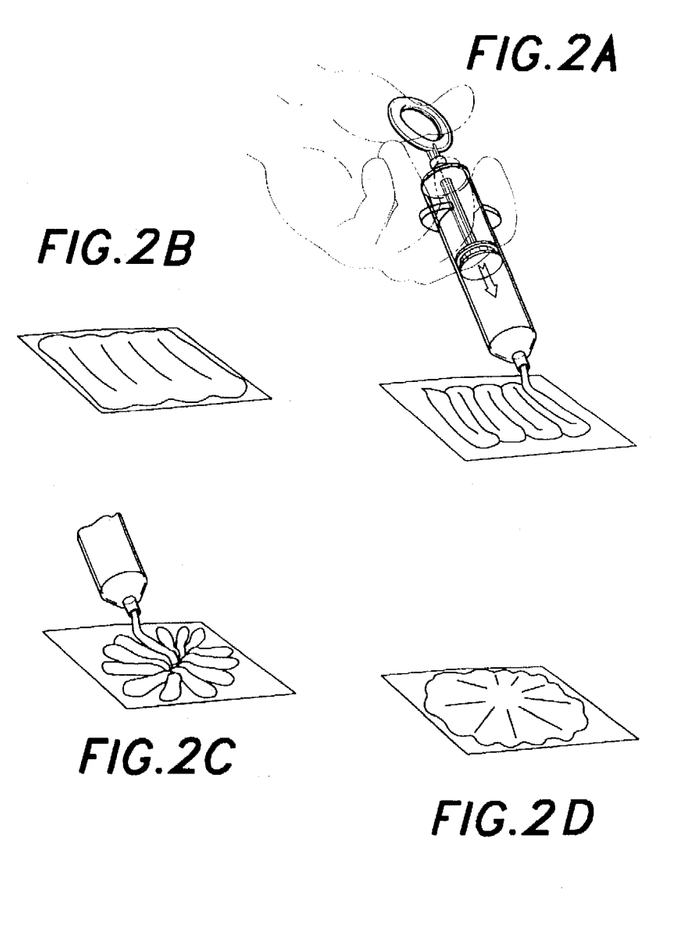

FIGS. 2(a) through (d) show a preferred technique for forming the film from the gel. Generally, the gel is extruded from a syringe S onto a preferably planar support. As shown in FIG. 2(a), the syringe may be moved so as to lay down a plurality of substantially parallel lines. When gelled into a film, the structure appears substantially as shown in FIG. 2(b). Alternatively, the gel may be extruded from a syringe in a sunburst pattern such as shown in FIG. 2(c). When the film is gelled, it appears as substantially shown in FIG. 2(b). The gel may be laid out in any desired pattern or by alternative apparatus that will orient the polymer in the planar direction, such as with a film casting knife or film extruder. The foregoing examples are merely illustrative and not intended to be limitative.

Such films are believed to consist of domains of oriented collagen. The oriented polymer domains help to control the thermally induced shrinkage of collagen films during welding.

After film formation, it was then incubated from substantially 34 to 37 C. to gel the collagen once again. Generally, no compression of the gel was required for this step since the collagen concentration was sufficiently high, from substantially 20 to 40 mg per ml. After gelling for 3 to 20 hours, the gel was washed with water and aqueous plasticizer solution, such as 1% sorbitol in water. The gel was then dried to a film, generally having a thickness from 1 to 7 mils, and subsequently cut into surgical patches, packaged and sterilized.

Another method to control collagen patch shrinkage during welding involves partial gelatin conversion of the collagen patch prior to welding. Since the shrinkage potential of collagen is relieved after denaturation to gelatin, "preshrinkage" of the fabricated collagen film can be performed. The oriented collagen film previously described, may be partially gelatinized. One method for converting the films to a state of partial or complete gelatin consists of the steps of:

1. Hydrating the films, such as in water to a weight 2 to 6 times their initial dry weight, 2. Heating the hydrated patches at a temperature sufficient to cause denaturation, such as by placing the patches in polystyrene containers which are floated on water at 90 to 95 C., 3. Remove the heated, hydrated patches upon observation of shrinkage of the films, such that minimal molten gelatin is created, and 4. Dry the films, such as by air drying, optionally followed by cross-linking of the films by exposure to saturated formaldehyde vapor for 15 minutes.

5. Size and cut the films into surgical patches, package, and sterilize for medical use.

Structural composites of collagen and non-thermally shrinking materials such as gelatin can be combined to provide patches with the good tissue welding properties of collagen but with only slight, if any, undesired mechanical deformation during welding. A gelatin composite film is fabricated to provide a biodegradable matrix for imbedded collagen particles by casting a gelatin solution with suspended collagen particles.

A method for forming a cast gelatin composite film, is as follows.

1. A 10% by weight aqueous slurry of fibrillar collagen was heated to boiling, through use of a microwave oven for three minutes, resulting in the denaturation of most of the collagen into gelatin. Residual collagen fibers were dispersed in the solution, though generally they were microscopic. The viscosity of the slurry decreased substantially when formed into the gelatin state.

2. The solution pH was measured, and adjusted to the range of 6 to 8 as necessary, through the addition of dilute acetic acid or sodium hydroxide.

3. The solution was cooled to a temperature of approximately 40 to 60 C., at which time the solution was cast onto a Teflon coated glass plate, via a knife blade. A thickness in the range from 1 mil to 500 mils can be used to provide a film of the appropriate dry thickness.

4. The film was then dried on the plate, by placing the plate and film in a 37 C. oven overnight.

5. The film was removed from the plate and crosslinked by exposure to saturated formaldehyde vapor, for 15 minutes.

6. The films were then cut into appropriately sized patches, packaged and sterilized for medical use.

A film formed from a 50 mil thick application of the heated solution became substantially 8 mils thick when dried.

The cast composite gelatin films described immediately above may be optionally coated with a hydrophobic barrier coating. In one method, a biocompatible, water resistant coating was formed with palmitic acid or lauric acid. In the preferred method, the films were dipped into 50 mg/ml solutions of the fatty acids in a solvent, such as chloroform, and dried. The film surface became waxy and slightly opaque. Weights of the sample showed approximately 0.3 mg of coating per square centimeter of the films. In a comparison hydration test, untreated films doubled in weight through rapid hydration in 15 seconds in saline solution at room temperature. The films treated with palmitic acid hydrated to less than ½ the weight, specifically, 44%, of the control sample. The lauric acid treated films hydrated to substantially ¼ of the control sample, specifically, 26% of the control sample weight.

Collagen has been found to be particularly useful for formation of the welds of this invention. Collagen has proved to have sufficient mechanical strength to provide a durable yet flexible weld which remains long enough to aid in tissue recovery. Further, collagen promotes ingrowth from the tissue 12, again promoting relatively rapid recovery. Finally, collagen is advantageous in being biodegradable and biocompatible.

Other patches or fusible structures may be used. For example, a mesh or mesh composite formed from polylactide or polyglycolide may be used. A fishnet structure, especially when filled with weldable collagen, might be useful, especially for procedures such as hernia repair. Gortex or other PTFE materials may be advantageously used, especially when formed with prepunched holes. Cellulose may be used for patch material, such as utilizing surgical suture material. Polypropylene patches such as formed from Marlex may be used.

The general method utilized in accordance with this invention is as follows. First, the patch is trimmed or shaped, if necessary to fit the surgical site, and then placed in contact with the tissue. Generally, the patch should be sized to be larger than the wound or incision, typically an area sufficient to give a 1–2 cm margin around the wound. Welding can be focused on the 1–2 cm margin, and in thinner patches welded across the entire area. The patch may be sized by cutting or by any other suitable method for sizing the patch.

After the patch has been placed on the tissue, energy is supplied to the patch. Sufficient energy must be supplied to the tissue to form a coagulum. Further, if holes or interlock vias 14 must be formed, sufficient energy is necessary to cause hole formation. Generally, it is preferable to limit the amount of energy delivered beyond that necessary to form the coagulum and optionally the holes, such that the structural integrity of the patch is retained and excessive tissue damage is prevented. In the preferred embodiment, it is desirable to raise the tissue temperature to substantially the boiling point of water. In this way, a desiccated tissue patch or coagulum is formed. In the preferred embodiment, the energy source comprises an RF inert gas coagulator, such as those commercially available from Valleylab, (Boulder, Co.), or Birtcher Medical Systems, (Irvine, Calif.). The most preferred gas is argon, though the other noble gases are acceptable. The use of inert gas RF energy sources is a form of "cold" heat which permits generating temperatures sufficient to form a coagulum, but avoids excessive tissue damage.

Once the energy has been supplied to the tissue such that a coagulum forms, a molten state exists, which permits the flow through the holes or interlock vias 14. When the coagulum cools and solidifies, a mechanical interlock is formed between the patch 10 and the coagulum 12.

It has been found that a particularly advantageous combination is the use of inert gas RF energy source with collagen patches. The combination provides for a uniquely strong but flexible weld in which the coagulum is in mechanical interlock with the holes formed in the patch but also, where there has been denaturing of the interface between the coagulum and the contacting surface of the collagen patch 10.

Figure 3A:
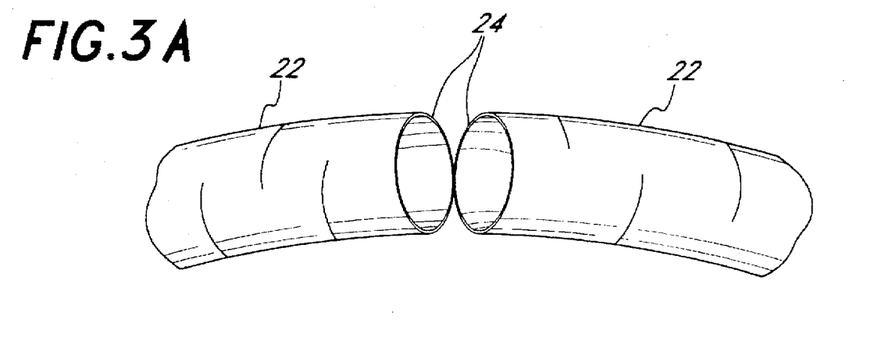
FIG. 3 is a drawing showing an expansible structure for use with potentially collapsible structures.
Figure 3B:
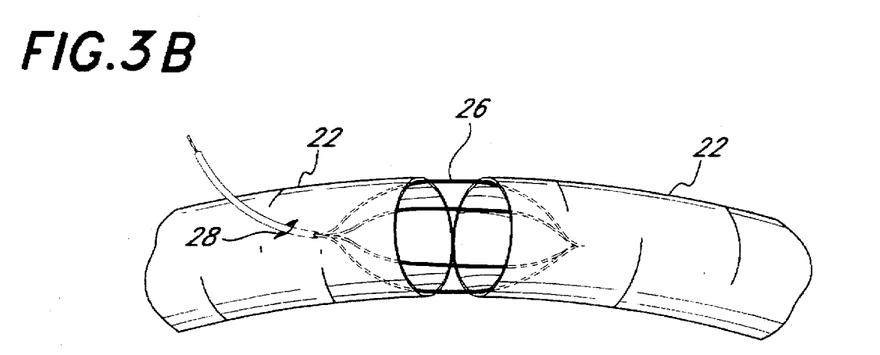
Figure 3C:
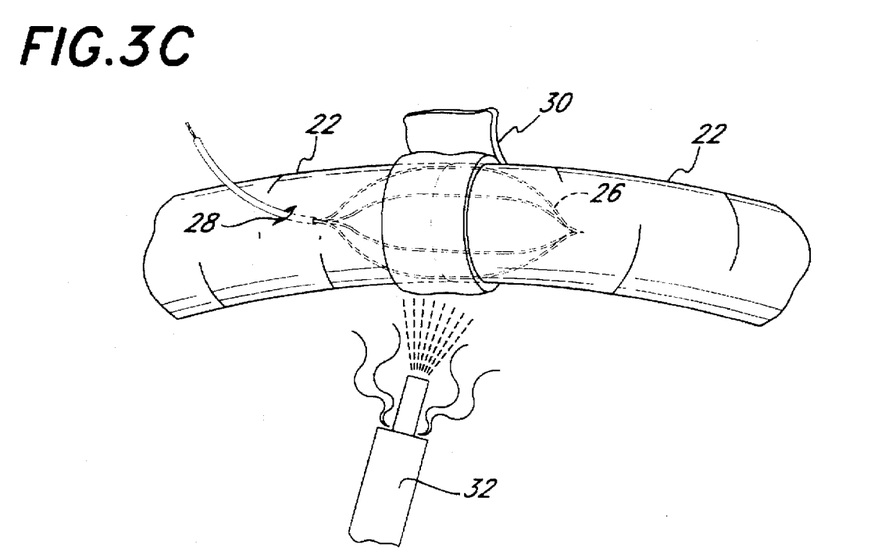

FIG. 3 shows use of the invention in connection with a bowel resection. FIG. 3A shows the bowel 22 having cut ends 24. To rejoin the sections, an expandable stent 26 is inserted preferably through a minor incision 28 in a portion of the bowel 22. The stent 26 is expanded to provide support to the potentially collapsible bowel sections 22. The ends 24 are placed in proximity with each other and a strip 30 of weldable material, such as a collagen strip, is placed around the ends 24. The welding tool 32, preferably an argon beam RF energy source, provides energy to the welding material 30. Once the welding material 30 has been welded under application of energy from the tool 32, the stent 26 may be removed through the incision 28.

Figure 4:
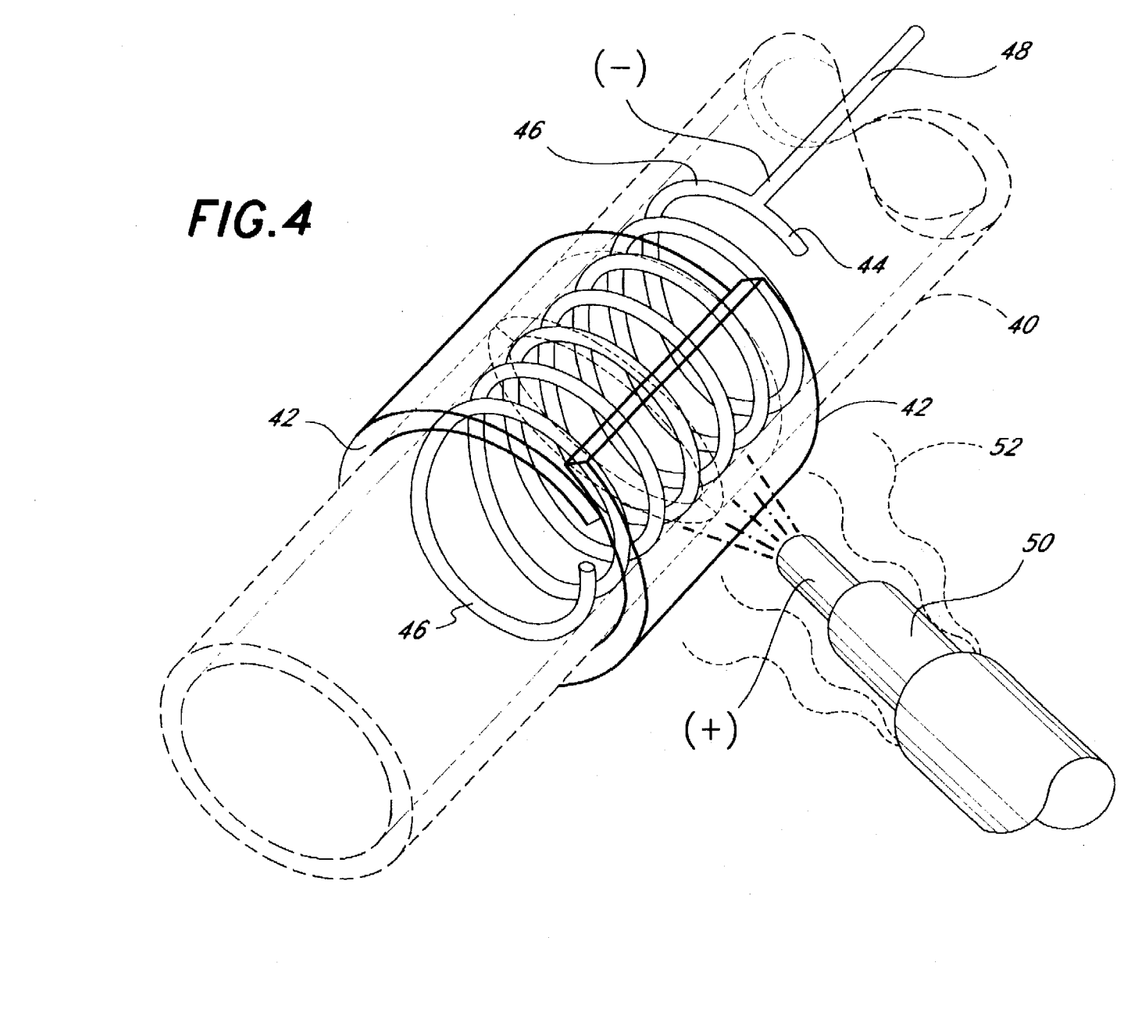
FIG. 4 is a perspective drawing in cutaway of a generally non-expansible support structure for use with a potentially collapsible structure.

FIG. 4 shows an alternative, generally non-collapsible, support structure for use in welding potentially collapsible structures. A biological structure 40, shown here to be generally cylindrical in shape, has wrapped around it the welding material 42. A support structure 44 is disposed within the interior of the biological material 40. In this embodiment, the support structure 44 is a generally helical structure 46 of sufficient length to provide support beneath the welding material 42 for the purpose of avoiding collapse of the biological material 40. Preferably, the support structure 44 includes a positioning member 48 which is connected to the generally helical portion 46. The energy source 50 provides a blanket of energy 52.

Figure 5:
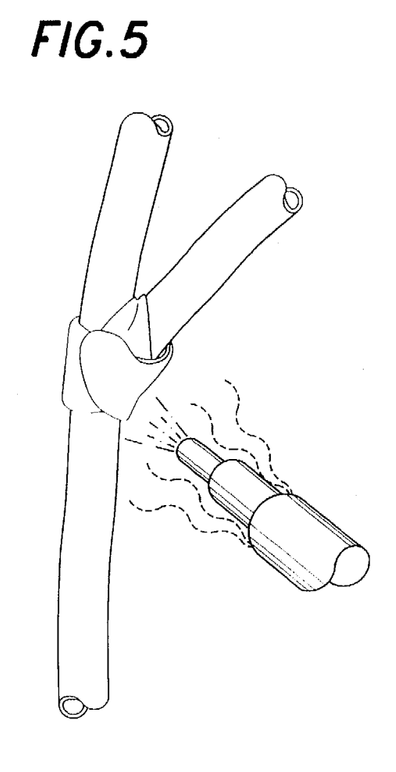
FIG. 5 is a side view of a patch secured to a side to end vessel anastomosis.

FIG. 5 shows a side view of a patch securing a side to end vessel anastomosis.

Figure 6A:
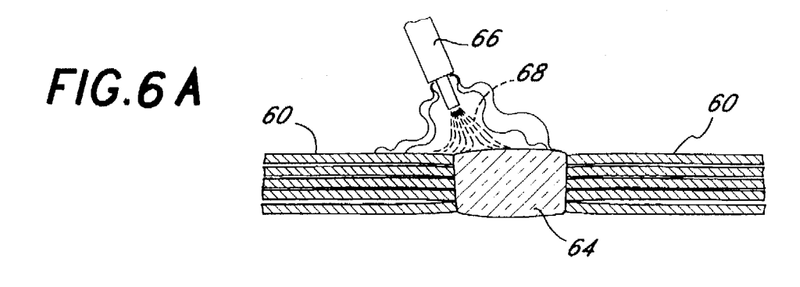
FIG. 6 is a cross-sectional drawing of a bridge structure adapted for use in tendon or ligament repair.
Figure 6B:
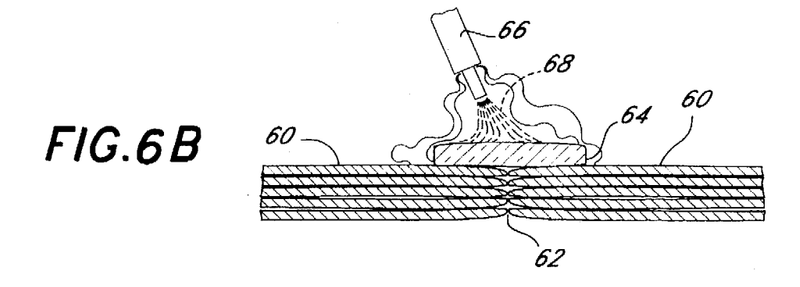
Figure 6C:
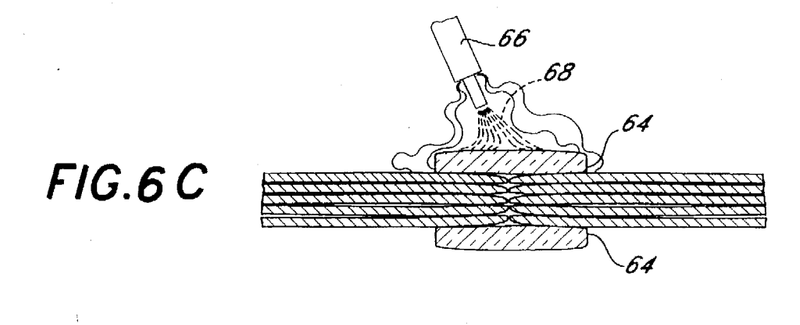

FIG. 6 shows the use of the invention in conjunction with the attachment or welding of structures such as tendons or ligaments. A biological structure 60 has ends 62 which are placed in adjoining position. A weldable material 64 is disposed adjacent the ends 62 to provide a weld or reconstruction. An energy source 66 provides energy plume 68. In one embodiment, the welding material 64 may be disposed substantially around the biological structure 60. In another embodiment, the weldable material 64 may be disposed as a bridge spanning the ends 62 of the biological material 60. In yet another embodiment, weldable material 64 may provide bridges on both sides of the ends 62.

Of particular advantage is the use of the invention to repair defects of the lung. The high expansion of the lung requires a flexible and strong bond with a gas-tight seal. The use of a patch welded over a lung, such as over a wound from tumor removal or a rough surface of the lung, provides a seal to close the wound and prevent air leakage. Additionally, a strip of weldable patch material could be used in conjunction with sutures and staples to provide additional sealing over the mechanical closures, for example, over the staple or suture line of a lobectomy. These techniques are useful in thoracic procedures including lung biopsies (e.g., wedge resection or local excision), lobectomies, and emphysema surgeries.

Experimental Results

Figure 7:
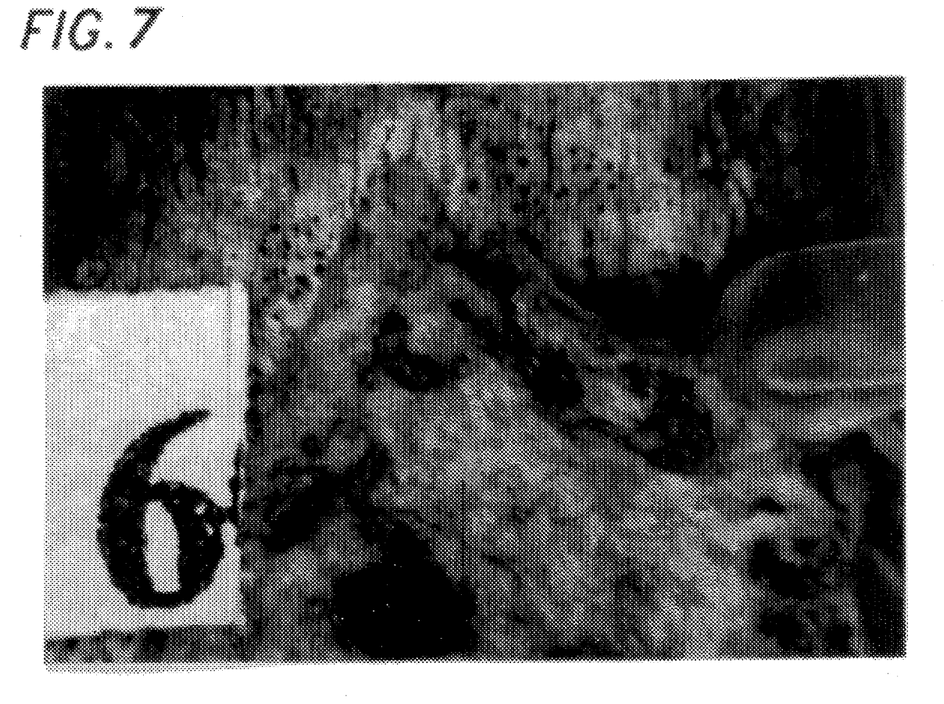
FIG. 7 is a photograph of a collagen patch welded to a section of heart muscle.

FIG. 7 is a photomicrograph of a collagen patch welded in-vitro onto a section of bovine heart muscle. The patch has been rendered opaque through the generation of coagulum through the patch by treatment with an argon coagulator. A folded portion of the patch on the right is untreated, and has a translucent appearance.

Figure 8:
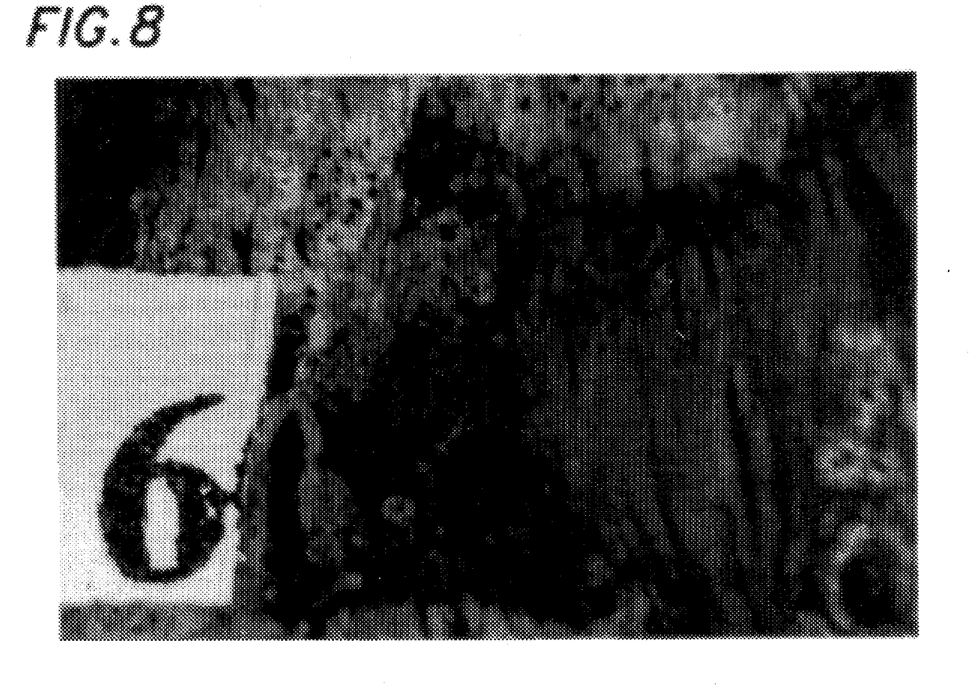
FIG. 8 is a photograph of the heart muscle after removing the welded collagen patch of FIG. 7.

FIG. 8 is a photomicrograph of the bovine heart muscle from FIG. 7 after removal of the adhered collagen patch. The patch border is evident by the lack of surface coagulum, with slight thermal damage to underlying tissue.

Figure 9:
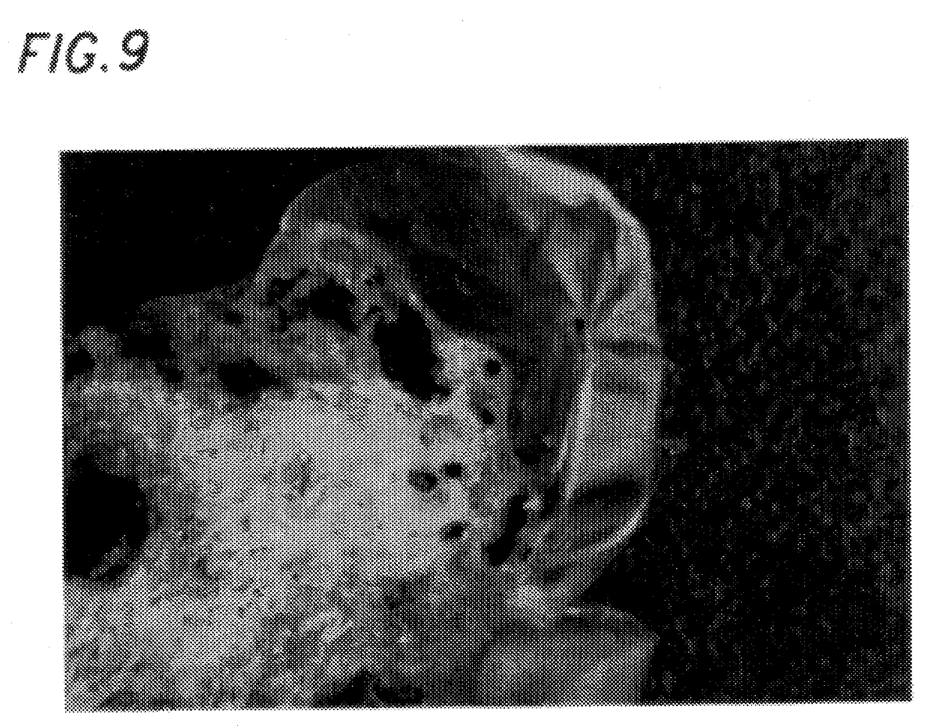
FIG. 9 is a photograph of the collagen patch removed from the heart muscle as shown in FIG. 7.

FIG. 9 is a photomicrograph of the removed patch from FIG. 7. The opaque area which was welded shows the coagulum generated by welding and dark holes which were created during the welding procedure. The unwelded portion of the patch is on the right, with a translucent appearance characteristic of collagen patches prior to welding.

Figure 10:
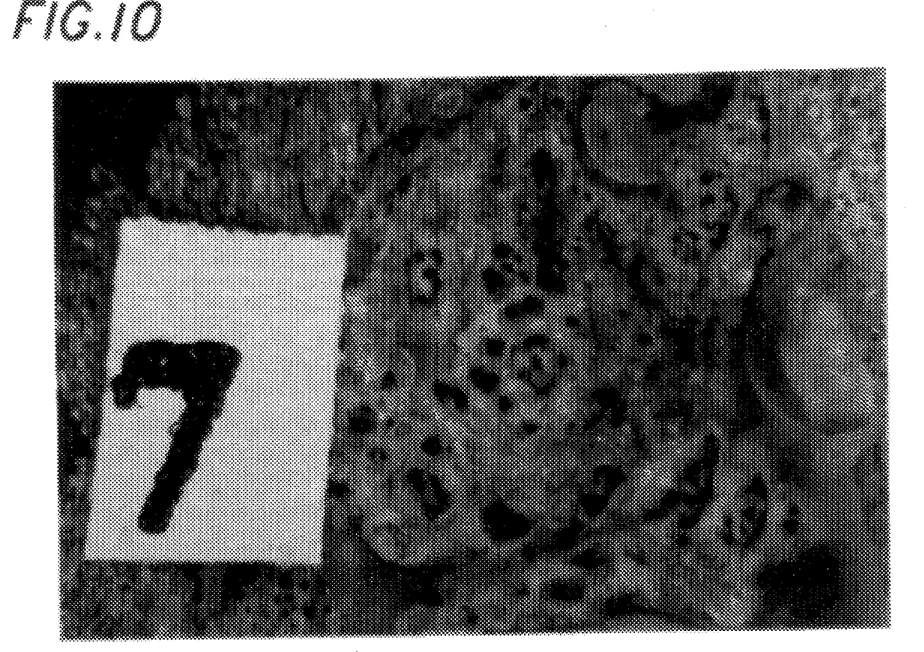
FIG. 10 is a photograph of a collagen patch welded to heart muscle.

FIG. 10 is a photomicrograph of a collagen patch welded in-vitro onto a section of bovine heart muscle. Opaque islands formed from the coagulum generated by the argon beam treatment are visible in the central portion of the patch, with unwelded edges.

Figure 11:
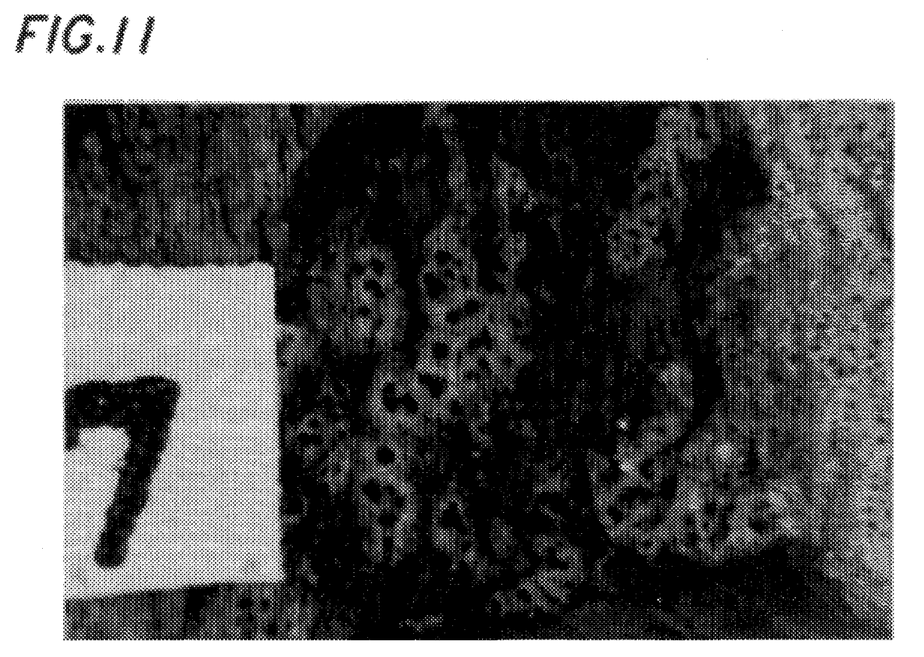
FIG. 11 is a photograph of the heart muscle after removing the welded collagen patch shown in FIG. 10.

FIG. 11 is a photomicrograph of the bovine heart muscle from FIG. 10 after removal of the adhered collagen patch. The patch border is evident by the lack of surface coagulum. The islands of coagulum in the center region are still evident, as they had interlocked strongly with the collagen patch.

Figure 12:
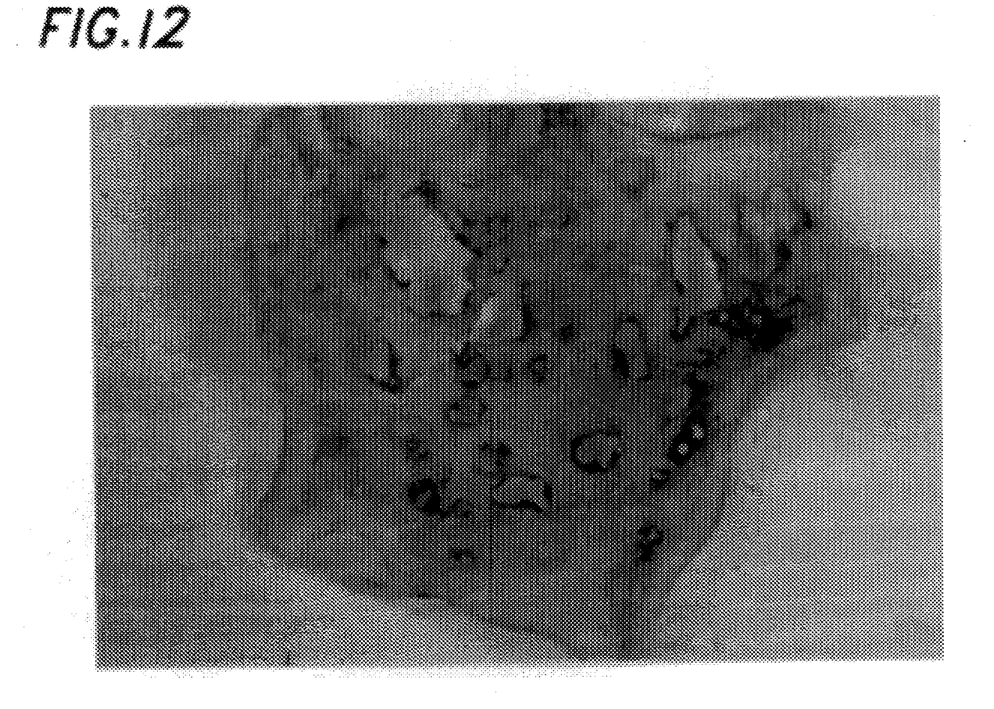
FIG. 12 is a photograph of the collagen patch after being removed from heart muscle as shown in FIG. 10.

FIG. 12 is a photomicrograph of the removed patch from FIG. 10. Dark and opaque areas are evident due to the coagulum generated by the underlying tissue during welding. Holes in the patch are visible, and were either generated by the argon beam treatment, or by the cohesive failure of the patch in strongly adhered regions during removal.

A collagen film was prepared to a thickness of 0.15 mm. The film was cut into a rectangular patch 2 cm by 1 cm in dimension. One end of the dry patch was placed on a sliced piece of beef heart tissue. An argon beam coagulator (Birtcher 6400; Birtcher Medical Systems, Irvine, Calif.), was applied for approximately 1 second per 4 mm², at 40 watts of power and a 4 liter/min argon gas flow. Holes approximately 0.2 to 0.5 mm in diameter were created in the patch, and the tissue underneath was converted to a molten phase which rapidly congealed, forming a coagulum. Inspection of the weld after saline irrigation showed most of the patch converted to gelatin as judged by transparency, with opaque collagen regions still visible in areas not subject to the argon beam. At magnifications of 10× to 30×, it appeared that the patch was bonded to the beef heart by being embedded and interlocked with the coagulum. The gelatinized regions of the patch were noted to be adherent to the beef heart. The end of the sample that was not welded to the tissue was bonded with cyanoacrylate glue to a 2×2 cm square of polystyrene sheet. On the beef heart sample, a similar square of polystyrene was glued to allow tension testing of the patch to tissue bond. The polystyrene tabs were placed in the jaws of a Instron Model 4202 mechanical testing apparatus. The shear strength of the weld was measured to be from 0.35 to 0.55 N/cm², at times limited by the cohesive failure of the patch material.

A partially gelatinized collagen film, being approximately 0.5 mm thick, was welded to a piece of beef heart tissue, utilizing an argon coagulator (Bard System 4400 and Beacon Labs Beamer 2). Welding was performed at 20 watts power and an argon flow rate of 4 liters per minute. Patches were welded dry and after 30 seconds of hydration in physiological saline. Dry patches tended to form holes through the patch and a flow of coagulum from the underlying tissue, with appreciable bond strength after 3 minutes of saline irrigation. The hydrated patches exhibited some curling as collagen was thermally converted to gelatin during welding. The patch material appeared to swell and partially melt and flow, giving a bond after saline irrigation, but weaker than the patch welded in a less hydrated state.

Films from the cast gelatin composite method were welded in the dry state onto beef heart tissue, and also after one minute of hydration in physiological saline, per the procedure of the preceding example. The films welded dry demonstrated holes formed and appeared bonded by interlocking with congealed coagulum. The hydrated films shrank slightly and appeared to bond by an integration of the flowed material of the patch and underlying tissue components. The samples of film coated with palmitic acid were also placed onto the heart tissue and welded, demonstrating no apparent loss in bond strength as compared to untreated samples after the 3 minute saline irrigation.

In a dramatic demonstration of the invention, approximately 2×3 cm patches from the oriented collagen film and gelatin-composite films described were applied over a 1.5 cm stab incision on the lung of an anesthetized pig. The patches were applied and welded at 40 watts with a Birtcher 6400 Argon Beam Coagulator. The energy was applied across the entire surface of the patches creating coagulum through the patch. Upon completion, the patches adhered to the lung surface, expanded with the lung, and provided a hemostatic and gas tight seal. The chest of the pig was closed and the animal recovered normally from the surgical procedure. After seven days, the animal was anesthetized and the chest opened. The lung patches had begun to bioresorb at least in part, but provided a healthy, healed lung surface that expanded with inflation and provided a fluid and gas tight seal as evident by irrigation with saline.

An electrocautery device was used to weld a patch in vitro as follows. A cast composite gelatin film formed from the method disclosed above was placed on a piece of beef heart tissue. A standard electrocautery device (Birtcher 6400; Birtcher Medical Systems, Irvine, Calif.) operated in standard electrocautery mode without the inert gas was used at 40 to 45 watts of power. The electrocautery tip was used gently on the patch surface to cauterize the tissues underneath the patch, causing holes to be formed through the patch and gelatinizing the patch material, while forming an interlocking coagulum from underlying tissues, similar to welding in the inert gas or argon mode. The holes formed in the patch were larger than those formed with the argon beam coagulator, but still allowed a tissue bond to the patch to be formed.

Although the invention has been described with respect to specific preferred embodiments, many variations and modifications may become apparent to those skilled in the art. It is therefore the intention that the appended claims be interpreted as broadly as possible in view of the prior art to include all such variations and modifications.

We claim:

1. A method for joining cylindrical biological structures, said method comprising the following steps:

drawing ends of the cylindrical biological structures together;

placing weldable material over said ends wherein the weldable material is selected from the group consisting of collagen, gelatin, albumin, fibrin and elastin; and applying energy to the weldable material while the ends of the cylindrical biological structures remain drawn together; denaturing or melting said weldable material and adjacent biological tissue of said biological structures with the applied energy to cause mixing of the denatured or melted weldable material and adjacent biological tissue, thus joining or restructuring said biological structures.

2. A method as in claim 1, wherein the cylindrical structures are hollow, further comprising disposing a support structure within the ends while the energy is applied.

3. A method as in claim 2 wherein the cylindrical structures are bowel having cut ends.

4. A method as in claim 2, wherein the support structure comprises an expandable stent or a helical support structure.

5. A method as in claim 1, wherein the weldable material is a collagen strip.

6. A method as in claim 1, wherein the energy is applied from an RF energy source.

7. A method as in claim 1 wherein the cylindrical structures are tendons or ligaments.

8. A method for repairing defects in the lung, said method comprising the following steps:

positioning weldable patch material over a wound in the lung; and applying energy to the patch material that results in denaturing or melting said weldable patch material and adjacent lung tissue to seal the wound and prevent air leakage therethrough wherein said weldable patch material is selected from the group consisting of collagen, gelatin, albumin, fibrin and elastin.

9. A method as in claim 8, wherein the wound results from a surgical procedure.

10. A method as in claim 9, wherein the surgical procedure is a lung biopsy, a lobectomy, or emphysema surgery.

* * * * *